(12) United States Patent
Malergue et al.

(10) Patent No.: US 11,666,917 B2
(45) Date of Patent: Jun. 6, 2023

(54) COLLECTION AND PREPARATION OF BLOOD SAMPLES FOR POINT-OF-CARE DIAGNOSTICS

(71) Applicant: Beckman Coulter, Inc., Brea, CA (US)

(72) Inventors: Fabrice Malergue, Marseilles (FR); Jean-Marc Busnel, Marseilles (FR)

(73) Assignee: Beckman Coulter, Inc., Brea, CA (US)

( * ) Notice: Subject to any disclaimer, the term of this patent is extended or adjusted under 35 U.S.C. 154(b) by 417 days.

(21) Appl. No.: 16/644,912

(22) PCT Filed: Aug. 31, 2018

(86) PCT No.: PCT/US2018/049196
§ 371 (c)(1),
(2) Date: Mar. 5, 2020

(87) PCT Pub. No.: WO2019/050802
PCT Pub. Date: Mar. 14, 2019

(65) Prior Publication Data
US 2021/0069703 A1    Mar. 11, 2021

Related U.S. Application Data

(60) Provisional application No. 62/554,225, filed on Sep. 5, 2017.

(51) Int. Cl.
*A61B 5/15* (2006.01)
*B01L 3/00* (2006.01)
(Continued)

(52) U.S. Cl.
CPC .... *B01L 3/50825* (2013.01); *A61B 5/150343* (2013.01); *A61B 5/150351* (2013.01);
(Continued)

(58) Field of Classification Search
CPC .......... B01L 3/50825; B01L 2300/042; B01L 2300/0832; A61B 5/150343;
(Continued)

(56) References Cited

U.S. PATENT DOCUMENTS

| | | | | |
|---|---|---|---|---|
| 5,145,646 A * | 9/1992 | Tyranski | .............. | G01N 35/025 422/547 |
| 6,319,209 B1 * | 11/2001 | Kriz | ................. | A61B 5/150343 600/583 |
| 7,456,024 B2 * | 11/2008 | Dahm | ................... | B01L 3/5635 436/164 |

(Continued)

FOREIGN PATENT DOCUMENTS

| | | |
|---|---|---|
| AU | 1754288 | 12/1988 |
| CN | 101002094 | 7/2007 |

(Continued)

OTHER PUBLICATIONS

"Canadian Application Serial No. 3,075,022, Response Filed Jan. 26, 2022 to Office Action dated Oct. 18, 2021", 12 pages.
(Continued)

*Primary Examiner* — Roy M Punnoose
(74) *Attorney, Agent, or Firm* — Schwegman Lundberg & Woessner, P.A.

(57) ABSTRACT

This disclosure is directed to methods and devices (300) associated with Point of Care medical testing and diagnostics. More specifically, methods and devices are described which provide a quick and streamlined way to prepare blood samples for analysis using flow cytometers, microscopes, and other analysis platforms. The benefits include a reduction in the time, resources, and expertise needed for preparing those blood samples without compromising the accuracy and efficacy of diagnosing diseases or identifying specific particulates from those blood samples.

16 Claims, 3 Drawing Sheets

(51) Int. Cl.
    *G01N 1/38*     (2006.01)
    *A61J 1/20*     (2006.01)
    *G01N 1/28*     (2006.01)

(52) U.S. Cl.
    CPC ....... *A61B 5/150755* (2013.01); *A61J 1/2093* (2013.01); *G01N 1/28* (2013.01); *G01N 1/38* (2013.01); *B01L 2300/042* (2013.01); *B01L 2300/0832* (2013.01)

(58) Field of Classification Search
    CPC ........ A61B 5/150351; A61B 5/150755; A61B 5/150022; A61J 1/2093; G01N 1/28; G01N 1/38
    USPC .......................................................... 422/64
    See application file for complete search history.

(56) References Cited

U.S. PATENT DOCUMENTS

| | | | |
|---|---|---|---|
| 2003/0215892 A1 | 11/2003 | Orfao | |
| 2005/0014273 A1* | 1/2005 | Dahm | B01J 19/249<br>436/45 |
| 2005/0196872 A1* | 9/2005 | Nguyen | A61B 5/150213<br>436/174 |
| 2009/0155838 A1* | 6/2009 | Hale | G01N 1/38<br>435/7.1 |
| 2010/0099115 A1* | 4/2010 | Mach | G01N 1/38<br>435/7.1 |
| 2013/0248045 A1* | 9/2013 | Williams | A61J 1/1412<br>206/525 |

FOREIGN PATENT DOCUMENTS

| | | |
|---|---|---|
| CN | 102224260 | 10/2011 |
| CN | 203101404 | 7/2013 |
| CN | 104010672 | 8/2014 |
| CN | 104136596 | 11/2014 |
| CN | 105556276 | 5/2016 |
| CN | 105606418 | 5/2016 |
| CN | 106879252 | 6/2017 |
| CN | 111194241 | 5/2020 |
| CN | 111194241 | 5/2022 |
| DE | 60032907 T2 | 10/2007 |
| EP | 0183804 | 11/1986 |
| GB | 1538196 | 1/1979 |
| GB | 2218076 | 11/1989 |
| JP | H0536364 | 5/1993 |
| JP | 2007527537 | 9/2007 |
| JP | 2020532739 | 11/2020 |
| WO | WO-2010036808 A1 | 4/2010 |
| WO | WO-2015189960 A1 | 12/2015 |
| WO | WO-2019050802 A1 | 3/2019 |

OTHER PUBLICATIONS

"Japanese Application Serial No. 2020-513541, Final Notification of Reasons for Refusal dated Feb. 25, 2022", with English translation, 3 pages.

"Canadian Application Serial No. 3,075,022, Office Action dated Oct. 18, 2021", 6 pages.

"Japanese Application Serial No. 2020-513541, Notification of Reasons for Refusal dated Mar. 11, 2021", w/ English Translation, 7 pgs.

"Specifications: Ready for use OptiLyse C Lysis Solution", Beckman Coulter Data Sheet, [Online] Retrieved from the Internet: <URL: https://www.be-cytometry.com/PDF/Datasheet/A11895. pdf>, (2006), 3 pgs.

"Canadian Application Serial No. 3,075,022, Office Action dated Apr. 22, 2021", 4 pgs.

"Chinese Application Serial No. 201880065284.9, Office Action dated Apr. 6, 2021", w/ English Translation, 24 pgs.

"Japanese Application Serial No. 2020-513541, Response filed Jun. 10, 2021 to Notification of Reasons for Refusal dated Mar. 11, 2021", w/ English claims, 11 pgs.

"Chinese Application Serial No. 201880065284.9, Response filed Jun. 17, 2021 to Office Action dated Apr. 6, 2021", w/English claims, 32 pgs.

"Indian Application Serial No. 202017014914, First Examination Report dated Jul. 20, 2021", with English translation, 5 pages.

"Japanese Application Serial No. 2020-513541, Notification of Reasons for Refusal dated Aug. 23, 2021", with English translation, 7 pages.

"Chinese Application Serial No. 201880065284.9, Office Action dated Sep. 24, 2021", with English translation, 17 pages.

Park, Young Sil, "Molecular Pathological Biology Experimental Technology Technical Guide", People's Military Medical Publishing House, With Concise Statement of Relevance, (May 31, 2015), 7 pages.

"International Application Serial No. PCT/US2018/049196, International Search Report dated Nov. 19, 2018", 7 pgs.

"International Application Serial No. PCT/US2018/049196, Written Opinion dated Nov. 19, 2018", 8 pgs.

"International Application Serial No. PCT/US2018/049196, International Preliminary Report on Patentability dated Mar. 19, 2020", 8 pgs.

"European Application Serial No. 18786073.9, Response to Communication Pursuant to Rules 161 and 162 filed Jan. 19, 2021", 19 pgs.

"Japanese Application Serial No. 2020-513541, Response Filed Nov. 22, 2021 to Notification of Reasons for Refusal dated Aug. 23, 2021", with English claims, 8 pages.

"Chinese Application Serial No. 201880065284.9, Response Filed Nov. 23, 2021 to Office Action dated Sep. 24, 2021", with English claims, 16 pages.

"Canadian Application Serial No. 3,075,022, Non Final Office Action dated Mar. 31, 2022", 4 pgs.

"Japanese Application Serial No. 2020-513541, Response filed May 12, 2022 to Final Notification of Reasons for Refusal dated Feb. 25, 2022", w English Claims, 6 pgs.

"Canadian Application Serial No. 3,075,022, Response filed May 13, 2022 to Non Final Office Action dated Mar. 31, 2022", w Claims, 8 pgs.

"Canadian Application Serial No. 3,075,022, Examiners Rule 86(2) Requisition Report dated Oct. 13, 2022", 5 pgs.

\* cited by examiner

COLLECTION AND PREPARATION OF BLOOD SAMPLES FOR POINT-OF-CARE DIAGNOSTICS

CROSS-REFERENCES TO RELATED APPLICATIONS

This application is a U.S. National Stage Filing under 35 U.S.C. § 371 from International Application No. PCT/US2018/049196, filed on Aug. 31, 2018, and published as WO 2019/050802 on Mar. 14, 2019, which application claims priority to U.S. Provisional Patent Application No. 62/554,225, filed on Sep. 5, 2017, the disclosures of both of which are incorporated by reference in their entirety.

BACKGROUND

Point-of-care testing involves medical diagnostic testing at or near the time and place of patient care. In some cases, point-of-care testing may require obtaining a blood sample from a patient and preparing it in a way that allows it to be accurately analyzed. For instance, reporters and reagents may be added to a tube containing the blood sample in order to stain certain particles present in the sample. A flow cytometer (or any other suitable imaging platform) can be used to analyze the sample contained in the tube in order to diagnose the patient.

The process of collecting and preparing the blood sample may require the time and expertise of numerous individuals, who may use various devices and materials for collecting and preparing the blood sample. For instance, a phlebotomist may have to extract a blood sample from the patient into a collection tube, while a lab technician later transfers a portion of the blood sample from the collection tube to a reaction tube, then adds reporters and reagents to the transferred portion of the blood sample for analysis. The complexity of the process results in increased demands on the time, resources, and knowledge needed to prepare blood samples for use in point-of-care testing, which can affect the speed and reliability in the test results.

BRIEF SUMMARY

This disclosure is directed to methods and devices associated with point-of-care medical testing and diagnostics. More specifically, methods and devices are described which provide a quick and streamlined way to prepare blood samples for analysis using various imaging platforms. Any suitable analysis platform, such as a flow cytometer or a scanning cytometer designed to analyze cells one-by-one, may be used with the blood samples prepared through the disclosed methods and devices.

To provide additional background, flow cytometers are devices which are typically used in cell characterization, cell counting, cell sorting, and biomarker detection. Cells or particles are fluorescently or otherwise labeled and suspended in a stream of fluid, which is passed through a tube that constrains the particles to pass in a single-file flow path. One or more lasers are directed at this flow path. The lasers interact with each particle to generate light patterns at varying wavelengths, which can be detected in order to analyze the way each particle emits fluorescence and scatters incident light from the lasers. In this manner, a flow cytometer allows multiparametric analysis of the physical and chemical characteristics of up to thousands of particles per second. However, a sample of cells or particles must first be prepared in a specific manner prior to analysis from a flow cytometer, such as by labeling certain particles in the sample with fluorescent reporters so they interact in a certain way with the lasers.

In some embodiments, a method is contemplated that involves first obtaining a fluid sample (e.g., blood) from a biological organism (e.g., a patient). As an example, a lancet can be used to prick the patient's finger, earlobe, heel, or other accessible part to release a small amount of blood from the patient. The method may further involve transferring the fluid sample onto a cap of a sample container, with the sample container having the cap and a sample container body. The cap may be configured to attach and detach from the sample container body. Thus, the cap may first be detached to allow the fluid sample to be transferred onto the cap.

The sample container body may come pre-loaded with reporters. The reporters may be fluorescent reporters that are configured to bind to certain particles within the fluid sample for diagnostic purposes. These reporters may come pre-loaded in the sample container body in a dried form. Once the cap is detached from the sample container body (e.g., to allow the fluid sample to be transferred onto the cap), one or more support reagents can also be added to the sample container body. The support reagent(s) may perform multiple functions, such as diluting and reconstituting dried reporters, collecting the fluid sample from the cap when cap is reattached to the sample container body, facilitating the staining of any particles within the fluid sample (e.g., by binding the reporters to those particles), and facilitating the lysis of red blood cells within the fluid sample in instances of whole blood analysis.

Once the fluid sample has been transferred onto the cap and the reagent added to the sample container body, the cap can be reattached to the sample container body to form a closed sample container. At this point, the sample container body may contain the reporters and the one or more support reagents that have been added. The fluid sample will be disposed on the cap. Inverting the closed sample container may cause the one or more reagents to collect the fluid sample from the cap, thereby allowing the fluid sample to interact with a reporter and the one or more reagents and form a mixture. This mixture can be analyzed using any analytical device of an imaging platform (e.g., a flow cytometer) by placing the sample container into the analytical device. In some cases, prior to feeding the sample container into the analytical device, the closed sample container has to be opened by separating the cap and the sample container body to extract a portion of the mixture from the sample container body.

This approach allows for a reduction in the time, resources, and expertise needed for preparing those blood samples without compromising the accuracy and efficacy of diagnosing diseases or identifying specific particulates from those blood samples.

One embodiment of the invention is directed to a method. The method includes transferring a fluid sample onto a cap of a sample container, the sample container comprising the cap and a sample container body. The method also includes attaching the cap to the sample container body to form a closed sample container, wherein the sample container body holds a reagent, and inverting the closed sample container to mix the fluid sample with reagent.

Another embodiment of the invention is directed to a sample container. The sample container includes a sample container body containing a dried reporter, wherein the dried reporter is configured to interact with a reagent to reconstitute the dried reporter and form a mixture. The sample container also includes a cap that is attachable and detachable from the sample container body, wherein a closed sample container is formed when the cap is attached to the sample container body, wherein the cap includes a surface configured to retain a fluid sample, and wherein the closed sample container is configured to be inverted to allow the mixture to collect the fluid sample on the cap without permitting the mixture to leave the closed sample container.

These and other embodiments of the invention are described in further detail below.

BRIEF DESCRIPTION OF THE DRAWINGS

The present disclosure is described in conjunction with the appended figures.

Figure 1:
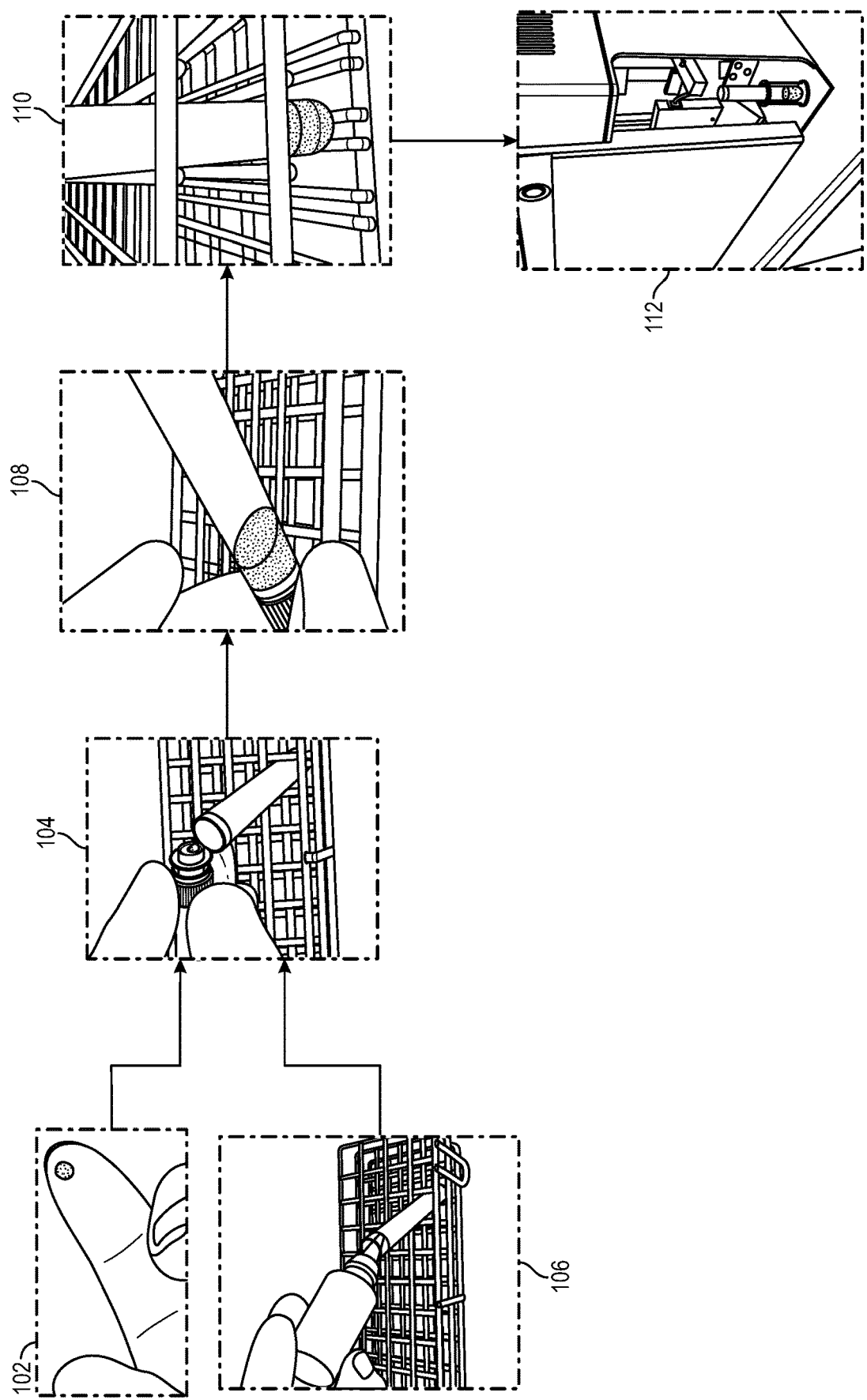
FIG. 1 illustrates a flow chart for a process of obtaining and preparing blood samples for analysis, in accordance with an embodiment of the present disclosure.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

INTRODUCTION

Historically, medical diagnostic testing (e.g., the detection or identification of diseases or antigens for a patient) involved sending blood samples (or other specimens) of a patient to a medical laboratory and waiting hours or days to learn the results, during which time care must continually be administered to the patient.

Point-of-care testing has improved that paradigm by allowing for medical diagnostic testing at the time and place of patient care, which increases the likelihood that the patient, physician, and care team will receive the test results quicker, which allows for better immediate clinical management decisions to be made.

Some point-of-care testing requires obtaining a blood sample (or some other suitable specimen or sample from the patient, such as urine) from the patient. The blood sample is then prepared in a manner that allows it to be accurately analyzed. For instance, a dye may be added to the blood sample in order to stain certain particles present in the sample, which allows those particles to be easily detected by an analysis platform that is then used to analyze the prepared blood samples. Any suitable analysis platform can be used. For instance, the analysis platform could be a flow cytometer, which uses flow in order to analyze cells one-by-one. Or the analysis platform may involve spreading out the cells in the blood sample onto a surface, which is then scanned by or viewed through a microscope.

However, the process of obtaining and preparing the blood sample for analysis can require considerable time, resources, and knowledge. For instance, the process typically involves a phlebotomist (e.g., a physician or nurse) withdrawing a sample of blood from a patient, and then transferring a portion, usually a measured portion, of the withdrawn blood sample into a cuvette or tube (e.g., a test tube). The tube is then capped and sent off to a lab technician, who will further prepare the blood sample before performing any analysis on the blood sample within the tube.

For instance, the technician may open the tube and mix in fluorescent reporters with the blood sample. Those reporters may bind to certain particles (such as blood cells) present in the sample, which allows those particles to be easily detected by an analysis platform. In some cases, the technician may also add to the tube a lysis solution configured to lyse some cells, such as red blood cells ("RBC"), in the sample. After the RBC lysis solution has been added to the tube, the tube may be incubated until complete lysis of the red blood cells is achieved. After the red blood cells in the sample have been lysed, the remaining cells, which may be of more immediate clinical interest, may be analyzed at a higher rate or with greater specificity. In addition, fluorescent reporters may more easily or completely bind to particles or cells of interest within the sample.

In embodiments of the invention, a "reagent" may include any suitable substance used for its chemical or biological activity. Reagents may be in liquid or dried form. Examples of reagents may include reporters (e.g., markers), support reagents such as lysis solutions, buffers, etc. A reporter may include a molecule that can comprise a chromophore such as, for example, fluorescein, rhodamine, Texas Red, phycoerythrin, Oregon Green, AlexaFluor 488 (Molecular Probes, Eugene, Oreg.), Cy3, Cy5, Cy7, and the like.

At this point, the technician may analyze the contents of the tube using any suitable imaging platform. For example, flow cytometry is routinely performed on processed whole blood samples; the technician may feed the tube into a flow cytometer to analyze the sample to identify or detect the presence of specific particles within the sample in order to diagnose the patient. Another type of platform can be a scanning cytometer.

However, as it can be seen, all these steps that are typically involved in obtaining and preparing the blood sample for analysis requires considerable time (e.g., to perform all the steps), resources/materials (e.g., needles, syringes, incubators, and so forth), and the expertise of multiple individuals (e.g., the physician/nurse and a lab technician). The minimum time needed for a physician or nurse to withdraw the blood sample into a tube and have a technician further prepare that blood sample (which may include incubation) can be at least 30 minutes to 1 hour. Since a goal of point-of-care testing is to receive quicker test results for immediate clinical management decisions to be made, a reduction in preparation time would be in furtherance of that goal.

Furthermore, since there are many steps and individuals involved in the typical approach to obtaining and preparing the blood sample for analysis, there is a greater potential for contamination, including contamination between samples.

After the physician/nurse caps the tube containing the blood sample, the technician is required to open up the tube again in order to further prepare the sample (e.g., to add the reporters and other reagents). Re-opening the tube may allow contaminants to enter the tube. Changing the procedure so that the tube only needs to be opened once would reduce the potential for contamination and allow for more accurate test results.

Various solutions have been proposed for reducing the time, materials, and resources needed to analyze whole blood samples. For example, automatic devices (e.g., AQUIOS CL Flow Cytometry System available from the Applicant) have been introduced to pierce the cap of a blood collection tube to mix reporters with the blood sample, thus supplanting part of the role of technicians. However, such devices do not address some of the other drawbacks previously mentioned. Some solutions (e.g., BD FACS PRESTO, available from Becton, Dickinson and Company) have been introduced for making it easier to obtain and prepare the blood sample. For example, a finger-prick blood drop can be used as a starting sample, and the blood drop is introduced into a complex cassette with capillary systems containing the reagents. However, the cassettes are adapted for analysis using imaging cytometry (not flow cytometry), the cost of the cassette is high due to its complexity and single-use nature, and the system as marketed is limited to a small variety of tests.

Accordingly, this disclosure describes methods and devices which provide a quick and streamlined way to obtain and prepare blood samples for analysis, especially using flow cytometry. The result is a reduction in the necessary time, resources, and expertise, as well as a reduction in the potential for contamination. In some cases, it may take as little as 15 minutes from extracting the blood sample from the patient until obtaining the test results.

FIGURES

Figure 2:
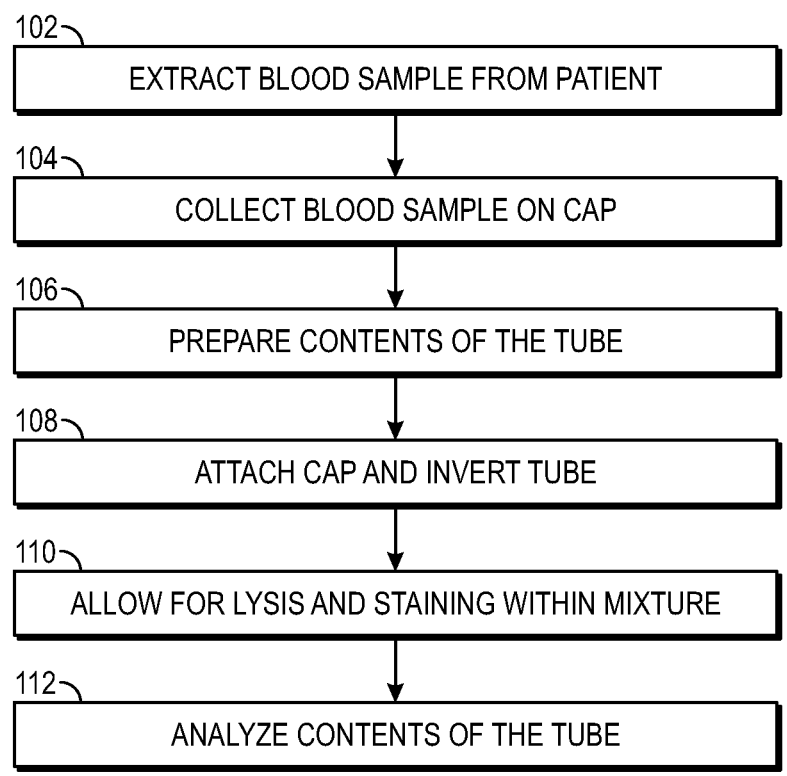
FIG. 2 illustrates a flow chart for a process of obtaining and preparing blood samples for analysis, in accordance with an embodiment of the present disclosure.

Both FIG. 1 and FIG. 2 illustrate flow charts for a process of obtaining and preparing blood samples for analysis, in accordance with an embodiment of the present disclosure. Accordingly, FIG. 1 and FIG. 2 are described together.

At step 102, a droplet of blood is extracted from a patient. In some embodiments, this blood droplet may have a volume of between 5 to 50 microliters. This blood droplet may be extracted using any appropriate method. In some embodiments, the blood droplet may be extracted from a patient by pricking the patient's fingertip with a lancet or needle. This collection of only a small droplet advantageously limits blood removal from the patient; this is of particular significance with pediatric or geriatric patients, but is also important where a patient's condition requires that many tests be performed. Further, the removal of only a small droplet reduces the use of consumables and reduces the production of potentially infectious medical waste. In other embodiments, blood may be withdrawn by conventional venipuncture with an aliquot subsequently transferred for analysis. The volume of the droplet of blood need not be precisely determined provided it contains sufficient cells for measurement. This is because flow cytometry measures characteristics of each cell individually, so that measurements are not tightly dependent on the concentration of cells. Further, the conditions within the tube are dominated by the much higher volume of support reagents as compared to blood so that variations in blood droplet volume do not significantly affect the environment surrounding each cell.

At step 104, the blood droplet may be collected by transferring the blood drop onto the inside of a clean cap that is configured to be coupled to a tube (e.g., flow cytometry tube or test tube) or cuvette. A suitable transfer method may be by touching the blood droplet on the finger or other body part to the cap. Alternatively, a portion of the blood may first be collected in a pipette or capillary tube and then deposited onto the inside of the cap. Any tube and cap combination may suffice, provided the analysis platform is configured to accept the tube, and provided the cap seals the tube sufficiently to permit mixing by inversion. For instance, some flow cytometers (e.g., a CytoFLEX Platform available from the Applicant) may accept a 1.5 mL microcentrifuge tube or an elastomer-stoppered tube to load processed sample. The cap may be at least partially wettable by the blood droplet so that the droplet adheres to the cap while the cap is positioned on the tube.

In some embodiments, steps 102 and 104 may be performed as a single step. For example, the cap may have a sterile lancet or needle disposed on it that can be used to prick the patient's fingertip in order to collect a droplet of blood at the tip of the needle.

At step 106, the contents of the tube may be prepared, which may include adding one or more reporters (e.g., a fluorescent marker) and/or one or more other reagents prior to use. Note that, in some embodiments, step 106 may be performed before steps 102 and/or 104. In other words, the contents of the tube may be prepared before extracting a blood droplet from a patient (e.g., prior to step 102). Or the contents of the tube may be prepared prior to collecting the blood droplet on the cap (e.g., prior to step 104). Thus, FIG. 1 illustrates step 106 occurring prior to step 104, whereas FIG. 2 illustrates step 106 occurring after step 104. In some embodiments, the contents of the tube may be prepared (e.g., by adding a recommend amount of reagent) extemporaneously before the blood is extracted from the patient.

In some embodiments, the tube may come already be preloaded with the reporters. The tube may be pre-loaded with reporters in different forms. For example, the reporters may be part of a liquid solution or cocktail stored within the tube. Or the reporters may be dried down and stored within the tube, such that the reporters would need to be suspended in liquid solution before use.

In some embodiments, a reporter may be a dye that selectively stains certain particles in the blood sample. In some embodiments, the dye may be used to assess biological status or function (e.g., for providing an indication about DNA, viability, metabolism, and so forth). In some embodiments, a reporter may be a bioreporter, which may include antibodies (conjugated with a dye or not) or other proteins, ligands, or peptides (conjugated with a dye or not) that can bind to cells or antigens in the sample. In some embodiments, the reporters may be bioluminescent or fluorescently-labeled antibodies configured to bind to specific antigens. Antibodies that are not conjugated with a dye may be used for blocking purposes by competitively binding to certain particles in the sample and preventing other reporters from attaching to those particles. In some embodiments, the reporter may be a fluorescently-labeled antibody specific for cell surface receptors or for internal cellular components, where the fluorescently-labeled antibodies are dried within the tube, such as the DuraClone reporters and combinations of reporters sold by the Applicant.

In some embodiments, one or more support reagent(s) can be added to the tube that is preloaded with reporters. The support reagent(s) may serve multiple functions. In some cases, a reagent may be in liquid form and it may dilute the reporters within the tube and reconstitute the reporters if they are dried. A support reagent may serve to collect the blood from the cap when the cap is affixed to the tube and the tube is inverted (described further in step 108). A support reagent may facilitate or allow the staining reaction to occur between reporters and blood cells within the sample.

In some embodiments, a support reagent may also facilitate or allow the lysis of red blood cells within the sample, such that no additional substances are required to be added to the tube before the tube is fed into the flow cytometer. In some embodiments, a support reagent used for lysing the red blood cells may be configured to lyse the red blood cells without impairing white blood cell integrity over a prolonged time. Such a support reagent may also be of neutral pH, or around neutral pH, in order to allow for a proper binding of antibodies.

In some embodiments, a support reagent may include VersaLyse Lysing Solution, a highly specific, gentle lysing solution used to lyse red blood cells from biological fluids and available from the Applicant. VersaLyse may be capable of performing all four functions mentioned above; diluting and reconstituting dried reporters, collecting the blood from the cap when the tube is inverted at step 108, facilitating the staining reaction, and facilitating the lysis of red blood cells within the sample. In some embodiments, a recommended volume of 500 µL of Versalyse Lysing Solution may be added to the tube.

In some embodiments, an anticoagulant (such as EDTA or heparin) may also be added to the tube. In some embodiments, the anticoagulant may be added as part of a liquid reagent (e.g., it may be pre-mixed with VersaLyse Lysing Solution). In other embodiments, the anticoagulant may be pre-loaded within the tube and dried down with the reporter(s).

For step 106, the task of adding reporters, reagents, and/or anticoagulants to the tube can be performed in numerous ways. For instance, classic pipetting using common lab devices can be performed to transfer reporters, support reagents (e.g., VersaLyse Lysing Solution), and anticoagulants from a bottle into the tube. This approach may require the use of pipetting devices for transferring exact amounts into the tube. Or, as an alternative, bottles of reporters, support reagents, and/or anticoagulants may be used that have a built-in dropper. However, this approach may be less precise for transferring exact amounts into the tube and may also be cumbersome if many tubes need to be prepared at once. Another alternative is to utilize pre-measured amounts of reporters, support reagents, and/or other materials such as anticoagulants, which may be supplied in unitized vials or containers (such as the container shown in FIG. 3). These containers may contain a precise amount of each component. For example, a container may be supplied pre-loaded with the recommended volume (500 µL) of VersaLyse Lysing Solution to add to the tube, and the same user that collects the blood drop on the cap can easily add the contents of the container to the tube. Thus, no pipette would be needed.

At step 108, the cap with the blood drop is affixed to the tube, which is then inverted. The reporters and support reagents may collect the blood drop from the cap to form a mixture. Thus, the contents of the tube will contain a mixture of the reporters, support reagents, anticoagulants, and the blood drop. At this point, a reaction (e.g., between the reporters, support reagents, and the blood cells) may start immediately, such that less than one minute has passed from the time that blood drop was extracted until the reaction time. This is preferable to the typical technique for collecting and preparing blood samples, which may involve the blood sitting in a collection tube for longer periods of time and leading to induced artifacts from cellular activation or de-activation as the blood sits.

At step 110, the red blood cells in the sample within the tube are lysed by the support reagent. The red blood cells, their contents, and/or particles within the sample may be stained by the marker.

At step 112, the tube may be used with the analysis platform (e.g., a flow cytometer) to analyze the contents of the tube. This may involve removing the cap from the tube right before feeding the tube into the flow cytometer, or the cap may be pierced by a needle of the flow cytometer in order to extract the contents of the tube for analysis.

Since the cap of the tube is only removed (or pierced) right before analysis, without the need to re-open the tube to add support reagents, there is less potential for contamination. Furthermore, the overall process may be much quicker, since there is no longer a need for a technician to measure out precise amounts of reporters, support reagents, and anticoagulant to add to the tube. The tube facilitates the easy collection of a blood sample and it may come pre-loaded with reporters and/or coagulant. A pre-measured amount of support reagent can be added to the tube along with the blood sample and then the tube can be capped to allow for the contents of the tube to mix. These steps do not require much knowledge or expertise and can be performed by the same user that extracts blood from the patient. This simplified and streamlined process has a reduced number of steps that can be performed by users with fewer qualifications, which reduces cost, the risk of errors, and the amount of time needed—in some cases, the entire process for collecting, preparing, and analyzing a blood sample can be reduced to 15 minutes.

Furthermore, this approach reduces the amount of medical device waste compared to the typical process for collecting and preparing a blood sample. This approach only requires a set gloves (worn by the user extracting the blood from the patient), a finger-prick device (e.g., a lancet or needle) for extracting the blood, and the capped tube. In contrast, the typical process may require multiple sets of gloves (worn by the user extracting the blood from the patient, as well as the technician preparing the tube), a needle and, depending on the blood collection system use, a syringe for extracting the blood from the patient, a collection tube for collecting the extracted blood, a reaction tube, and pipette tips (or similar pipetting devices) for measuring out blood, reporters, and support reagent into the reaction tube. Thus, this approach has the benefit of reducing the time, materials, and expertise needed to collect and prepare a blood sample for analysis in point-of-care diagnostics.

Finally, this approach may still provide accurate test results and diagnosis from the blood sample, even when a small amount of blood is taken. Flow cytometry may be used to measure the mean fluorescent intensities of each population of cells, stained by each type of reporter. A limited volume of blood allows an accurate measurement only on a population of cells that is not too rare. In practice, there would need to be at least 100 cells of a population in the sample in order for an accurate measurement to be obtained. This can be achieved in a 5 µL blood sample (50 000 WBC) analyzed for 2 minutes (at a flow rate of 1 µL/s=120 µL=¼ of the sample is analyzed=12500 cells) for populations that represent down to 1% of all the white blood cells. Thus, the small amount of blood required to be collected is very reasonable and allows most of the current point-of-care testing and analysis to be performed. The other measurement is the proportion of cells (e.g., of different populations), relative to each other, which also can be done with the same accuracy considerations as above.

Figure 3:
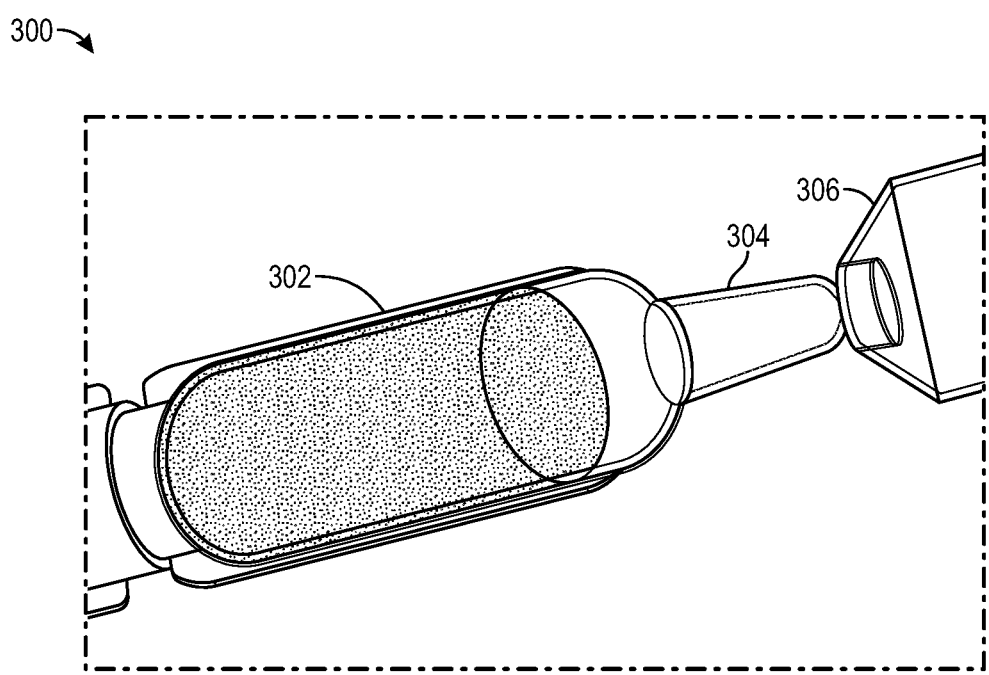
FIG. 3 illustrates a unitized vial of support reagent, in accordance with embodiments of the present disclosure.

FIG. 3 illustrates a unitized vial of support reagent, in accordance with embodiments of the present disclosure.

In some embodiments, the tubes used to collect blood samples may come with unitized vials or unitized containers of support reagent, such as container 300 shown in the figure. Thus, the task of adding a reagent to the tube (e.g., at step 106 shown in FIGS. 1 and 2) may involve opening the unitized container of reagent and pouring the reagent into the tube before disposing of the empty container.

In some embodiments, the container 300 may be a squeezable unit-dose container with an integral dropper tip (such as containers used to store and deliver Collyre Bleu Eye Drops; similar containers are commercially available from James Alexander Corporation). The container 300 may have a body 302 in which the contents are held. There may be a reduced diameter tip 304 disposed on the body 302 that is hollow and permits the contents of the container 300 to flow out when pressure is applied to body 302. Attached to the tip 304 may be a cap 306, which can be ripped or twisted off in order to expose the opening of the tip 304 for the contents to be dispensed.

Alternative Embodiments

In some embodiments, the tube may come pre-loaded with both reporter(s) and support reagent(s).

In some embodiments, the tube may come pre-loaded with both reporter(s) and support reagent(s) that are initially separate but are allowed to mix together when the cap of the tube is taken off. For instance, the tube may initially contain dried reporters and a liquid support reagent (e.g., VersaLyse Lysing Solution), with the liquid support reagent held in a compartment separated from the reporters. When a user opens the cap of the tube (e.g., in order to collect the blood drop), the compartment containing the liquid support reagent may be broken which releases the liquid support reagent to mix with the reporters.

The previous descriptions provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have also included additional steps or operations not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope if the invention.

What is claimed is:

1. A method comprising:
   transferring a blood sample onto a cap of a sample container, the sample container comprising the cap and a sample container body;
   attaching the cap to the sample container body to form a closed sample container, wherein the sample container body holds a reagent comprising a reporter and a support reagent, the support reagent comprising a red blood cell lysis solution; and
   inverting the closed sample container to mix the blood sample with the reagent.

2. The method of claim 1, wherein the reporter includes a labeled antibody.

3. The method of claim 1, wherein the reporter is dried within the sample container body, and wherein the method further comprises adding the support reagent to the sample container body.

4. The method of claim 1, further comprising analyzing at least a portion of the mixture of the blood sample and the reagent using an analysis device.

5. The method of claim 1, further comprising:
   analyzing a mixture of the blood sample and the reagent with an analytical device, the analytical device being a flow cytometer.

6. The method of claim 1, further comprising:
placing the closed sample container in an analytical device.

7. The method of claim 1, wherein the blood interacts with the reagent to lyse one or more red blood cells in a mixture and wherein the blood interacts with the reporter to attach the reporter to an unlysed cell.

8. A sample container comprising:
- a sample container body containing a dried reporter, wherein the dried reporter is configured to interact with a support reagent to reconstitute the dried reporter and form a mixture, the support reagent comprising a red blood cell lysis solution;
- a cap that is attachable and detachable from the sample container body, wherein a closed sample container is formed when the cap is attached to the sample container body, wherein the cap includes a surface configured to retain a blood sample, and wherein the closed sample container is configured to be inverted to allow the mixture to collect the blood sample on the cap without permitting the mixture to leave the closed sample container.

9. The sample container of claim 8, wherein the sample container body is configured to be inserted into a flow cytometer.

10. The sample container of claim 8, wherein the reporter includes a labeled antibody.

11. The sample container of claim 8, wherein the mixture is configured to interact with the blood by lysing one or more red blood cells in the blood and attaching the reporter to an unlysed cell.

12. The sample container of claim 8, wherein the dried reporter is configured to interact with a pre-measured amount of the support reagent.

13. The sample container of claim 12, wherein the pre-measured amount of the support reagent is dispensed from a unitized vial or container.

14. The sample container of claim 8, wherein the support reagent comprises at least 500 µL of the red blood cell lysis solution.

15. A method comprising:
- transferring a blood sample onto a cap of a sample container, the sample container comprising the cap and a sample container body that is preloaded with a reporter prior to the transferring of the blood sample onto the cap;
- before or after the transferring of the blood sample onto the cap, adding a support reagent from a unitized vial or container to the sample container body comprising the preloaded reporter to dilute and/or reconstitute the reporter, wherein the support reagent comprises a red blood cell lysis solution;
- attaching the cap to the sample container body to form a closed sample container, wherein the sample container body holds a reagent comprising the reporter and the added support reagent; and
- inverting the closed sample container to mix the blood sample with the reagent.

16. The method of claim 15, wherein an amount of the reporter preloaded in the sample container body is configured to interact with a pre-measured amount of the support reagent, wherein the support reagent added from the unitized vial or container to the sample container body is the pre-measured amount of the support reagent.

* * * * *